United States Patent [19]

Lidert

[11] Patent Number: 5,391,779
[45] Date of Patent: Feb. 21, 1995

[54] STABLE EXTRACTS FROM NEEM SEEDS

[75] Inventor: Zev Lidert, Doylestown, Pa.

[73] Assignee: Rohm and Haas Company, Philadelphia, Pa.

[21] Appl. No.: 920,237

[22] Filed: Jul. 27, 1992

[51] Int. Cl.⁶ .............................................. C07C 1/00
[52] U.S. Cl. ........................... 514/453; 554/183; 554/14; 424/195.1; 504/101
[58] Field of Search ............... 554/14, 183; 514/453; 424/195.1; 71/88

[56] References Cited

U.S. PATENT DOCUMENTS

| | | | |
|---|---|---|---|
| 4,325,883 | 4/1982 | Jones et al. | 554/182 |
| 4,325,885 | 4/1982 | Jones et al. | 554/182 |
| 4,556,562 | 12/1985 | Larson | 424/195.1 |
| 4,943,434 | 7/1990 | Lidert | 424/195.1 |
| 4,946,681 | 8/1990 | Walter | 424/195.1 |

Primary Examiner—José G. Dees
Assistant Examiner—Deborah D. Carr
Attorney, Agent, or Firm—Clark R. Carpenter

[57] ABSTRACT

A neem seed extract containing azadirachtin with improved stability has been developed using a process involving dissolution of the crude neem seed extract in a polar solvent and removal of impurities by precipitation and/or treatment of the extract with an oxidizing agent. The resulting extract, optionally formulated as a wettable powder, is a useful insecticide for the control of foliar pests.

10 Claims, No Drawings

STABLE EXTRACTS FROM NEEM SEEDS

FIELD OF THE INVENTION

This invention relates to stabilized extracts of the seeds of the neem tree (*Azadirachta indica* Juss.) which provide materials useful as insecticides, compositions containing such extracts and methods of their use.

BACKGROUND OF THE INVENTION

The search for compositions which have a combination of excellent insecticidal activity and desirable low toxicity to plants and mammals is a continuing one because of factors such as the desire for compounds exhibiting greater insecticidal activity, better selectivity, low environmental impact, low production cost and effectiveness against insects resistant to many known insecticides.

Various parts of the neem (or nim) tree have long been used in India for their reputed medicinal or insecticidal properties. This subtropical tree is native to the arid regions of India, Pakistan, Sri Lanka and parts of Southeast Asia and Africa.

Although all parts of the neem tree appear to have natural resistance to pests and diseases, the seeds appear to have the greatest resistance. Formulations and extracts of the seeds have been shown to be effective against many species of crop pests including gypsy moths, Japanese beetles, aphids, tobacco budworms and boll weevils. For example, see *Chem. and Engineering News*, May 27, 1985, pp. 46–51 and U.S. Dep. Agric., Agric. Rev. Man., ARM-NE-4. Neem seed extract is considered to be a broad-spectrum insecticide.

While neem seed extract has been shown to be active as an insecticide, it has not come into common use because of the known instability of the formulated extract. Moreover, undesirable aflatoxins, arising from fungal infection of the seed, may be present in the extracts.

Although laboratory scale procedures resulting in extract preparations containing over 25% azadirachtin have been described in the literature, a practical, economical and scalable method has been lacking.

Prior processes for obtaining crude neem extracts typically comprised the steps of:
  a) extracting the ground seed with a polar organic solvent such as methanol or ethanol followed by filtration,
  b) removing the solvent from the filtrate by evaporation under reduced pressure to yield a dry extract,
  c) dissolving the dry extract in a mixture of a water-immiscible polar organic solvent, such as ethyl acetate, and aqueous saturated sodium chloride solution and
  d) separating the organic layer, drying and evaporating the solvent to yield the semi-pure extract.

Such prior processes result in extracts containing a significant portion of hydrophobic organic impurities and no more than 10% azadirachtin. Higher purity preparations have been described but they require uneconomical, non-scalable chromatographic steps subsequent to those steps described above.

Several attempts have been made by various workers with the objective of removing the hydrophobic materials without resorting to chromatography. For example, *Journal of Liquid Chromatography*, 10 (6), 1151 (1987) shows an attempt to purify a crude methanolic extract by dissolving the extract in 50% aqueous methanol and then extracting the resulting solution with hexane. Other authors have described the removal of oil from the ground seed with a non-polar solvent such as hexane prior to the polar solvent extraction. However, these methods are not efficient since the crude methanolic or ethanolic extracts, apart from hexane soluble oils, also contain large quantities of hydrophobic impurities which are only sparingly soluble in non-polar solvents such as hexane.

In U.S. Pat. No. 4,556,562, an aqueous storage-stable neem seed extract composition is disclosed. In U.S. Pat. No. 4,946,681, a method is disclosed for stabilizing an alcoholic neem seed extract by removing water with molecular sieves.

Notwithstanding the above advances, there remains a need for an economical, stable composition effective to control pests, preferably a composition which is also free of aflatoxins.

SUMMARY OF THE INVENTION

It has now been discovered that an extract containing azadirachtin with improved stability can be prepared.

Simple alcoholic neem seed extracts as known in the art (U.S. Pat. No. 4,556,562) can be purified by a scalable method which yields extracts containing over 25% of azadirachtin. These extracts have improved stability when compared with less pure extracts containing 15% or less of azadirachtin.

Additionally, the stability of the extracts has been improved by treatment of the extract with a mild oxidizing agent such as alkaline solution of hydrogen peroxide. Moreover, the extracts which have been treated with hydrogen peroxide are also essentially free of aflatoxins which might be present in extracts from seeds contaminated with *Aspergillus niger*.

In addition, when extracts as described in U.S. Pat. No. 4,943,434 are treated with a mild oxidizing agent as described above, they are more easily hydrogenated to yield an extract containing dihydroazadirachtin with improved stability.

DETAILED DESCRIPTION OF THE INVENTION

It has now been found in this invention that crude neem seed extracts can be efficiently purified to yield extracts containing azadirachtin with enhanced stability using a scalable process which comprises:
  a) deoiling ground neem kernels by stirring with hexane followed by filtration to obtain a deoiled cake or, alternatively, by mechanically extruding the oil and optionally extracting the oil residue with hexane to obtain a deoiled cake,
  b) extracting the deoiled cake with methanol followed by filtration,
  c) removing the methanol to obtain a dry extract,
  d) dissolving about 3 parts of the dry extract in about 7 parts of methanol on a weight/weight (w/w) basis,
  e) Adding water preferably with stirring to a final ratio of about 35/65 methanol/water on a volume/volume (v/v) basis,
  f) Separating the aqueous methanolic phase from any solid impurities,
  g) Diluting the aqueous methanolic mixture with a saturated aqueous salt solution, preferably a sodium chloride solution,
  h) Extracting the dilute solution with a water immiscible solvent, such as ethyl acetate, and i) Drying the organic solution and, if desired, removing the solvent.

In another embodiment of this invention, crude neem seed extracts can be efficiently purified to yield extracts of higher purity and enhanced stability using a scalable process which comprises:

a) Evaporating a solution of crude neem extract in methanol obtained in Step b above to a concentrate containing over 65% volatiles, b) Adding water dropwise with stirring to a final ratio of between 5/95 methanol/water (v/v) to 45/55 methanol/water (v/v), preferably to a final ratio of 35/65 methanol/water (v/v), and c) Treating the resulting solution as described above by Steps f–i.

Additional stabilization of the extract is achieved by treating a neem extract in a solvent with an oxidizing agent such as an alkaline solution of hydrogen peroxide, an alkyl peroxide, for example di-n-butyl peroxide, an acid peroxide, for example perbenzoic acid, sodium percarbonate or the like. Preferred solvents for this reaction are polar organic solvents such as ethyl acetate or butyl acetate. A preferred oxidizing agent is hydrogen peroxide. A preferred base used with the hydrogen peroxide is saturated sodium bicarbonate solution.

The extracts of this invention are less susceptible to azadirachtin decomposition. When treated extracts of this invention and non-treated extracts were placed in an oven at 54° C. for several weeks and then tested to determine the azadirachtin content, it was found that the precipitation of the hydrophobic impurities by water from the methanolic solution of the crude extract and/or treatment with an alkaline solution of hydrogen peroxide significantly reduced the rate of decomposition of azadirachtin in the extract. It was also found that the precipitation of the hydrophobic impurities by water from the methanolic solution of the crude extract and/or treatment with an alkaline solution of hydrogen peroxide significantly reduced the content of sulfur in the extract.

The resulting extracts contain from about 1% to about 85% of azadirachtin and preferably from about 25% to about 45% of azadirachtin.

The stable extracts of this invention are also advantageously used in the preparation of storage stable formulations and compositions. Examples of the preparation of compositions and formulations can be found in the American Chemical Society publication "Pesticidal Formulation Research," (1969), Advances in Chemistry Series, 86 and the Marcel Dekker, Inc. publication "Pesticide Formulations," (1973), Wade Van Valkenburg editor. In these compositions and formulations, the active substance is mixed with conventional inert agronomically acceptable (i.e., plant compatible and/or pesticidally inert) diluents or extenders such as solid types usable in conventional compositions or formulations as is well known in the art. If desired, adjuvants such as surfactants, stabilizers, antifoam agents and antidrift agents may also be added.

Examples of compositions and formulations according to this invention are those known in the art and include aqueous solutions and dispersions, oily solutions and oil dispersions, pastes, dusting powders, wettable powders, emulsifiable concentrates, flowables, granules, baits, invert emulsions, aerosol compositions and fumigating candles.

The compositions and formulations are prepared in a known manner. For example, the active compounds are extended with conventional dispersible liquid diluent carriers and/or dispersible solid carriers. If desired, carrier vehicle assistants can be used such as conventional surface-active agents including emulsifying agents and/or dispersing agents whereby, for example, organic solvents may be added as auxiliary solvents in the case where water is used as a diluent.

Adhesives such as carboxymethyl cellulose and natural and synthetic polymers, for example gum arabic, polyvinyl alcohol, polyvinyl cellulose and polyvinyl acetate, in the form of powders, granules or latices can be used in the formulations to improve the adherence of the pesticide. Furthermore, a lubricant such as calcium stearate or magnesium stearate may be added to a wettable powder or to a mixture to be granulated.

The stabilized extract of the present invention may be employed alone and/or with such solid and/or liquid dispersible carrier vehicles and/or with other known compatible active agents, especially plant protection agents such as other insecticides, arthropodicides, nematicides, fungicides, bactericides, rodenticides, herbicides, fertilizers, growth-regulating agents, synergists and the like, if desired, or in the form of particular dosage preparations for specific applications made therefrom, such as solutions, emulsions, suspensions, powders, pastes and granules which are thus ready for use.

As concerns commercially marketed preparations, these generally contemplate carrier composition mixtures in which the stabilized extract is present in an amount substantially between 0.1% and 99% by weight and preferably between about 1% and 75% by weight of the mixture.

Some formulations are capable of confering an additional stabilizing effect on azadirachtin in the formulated form, possibly due to dispersion, protection from humidity, sunlight and the like.

The stabilized extract formulations can be applied as sprays by methods commonly employed such as conventional high-gallonage hydraulic sprays, low gallonage sprays, ultra low volume sprays, airblast sprays, aerial sprays and dusts.

Furthermore, the present invention contemplated methods of selectively killing, combatting or controlling pests which comprise contacting insects with a correspondingly combative or toxic amount (i.e., an insect controlling or an insecticidally effective amount) of the stabilized extract of the invention alone or together with a carrier vehicle (composition or formulation) as noted above. The term "contacting" as employed in the specification and claims of this application is to be construed as applying to at least one of (a) such insects and (b) the corresponding habitat thereof (i.e., the locus to be protected, for example a growing crop or an area where a crop is to be grown) the active compound of this invention alone, as a constituent of a composition or formulation or as a constituent of a composition or formulation containing other insecticides or fungicides.

It will be realized, of course, that the concentration of the particular stabilized extract utilized in admixture with the carrier vehicle will depend upon such factors as the type of equipment employed, method of application, area to be treated, types of pests to be controlled and degree of infestation. In addition to the aforementioned ingredients, the preparations according to the invention may also contain other substances commonly used in preparations of this kind.

The following examples are presented to illustrate the invention and are not to be construed as limiting in scope. All parts and percentages are by weight unless otherwise indicated.

EXAMPLE 1

Preparation of Extract 1 Containing Unstabilized Azadirachtin

Destoned neem seeds, 1027 kilograms (kg), were deoiled using first a standard mechanical oil expeller and then by extraction with hexane in a standard counter-current Crown-Iron solvent extractor. Using the same solvent extractor, the 701 kg of deoiled seed was then extracted with methanol at a ⅓ ratio of seed/methanol (w/w).

The dilute methanolic extract was stripped to give 70 kg of semi-solids which were then transferred to a kettle containing 160 kg of brine and 160 kg of ethyl acetate. After 0.5 hour of mixing, the phases were allowed to separate. The upper organic phase then was washed with 40 kg of brine, dried over 2 kg of magnesium sulfate, filtered and stripped to give 13 kg of Extract 1 containing 1.3 kg (10%) azadirachtin. The azadirachtin in this extract rapidly decomposed at room temperature.

EXAMPLE 2

Preparation of Extract 2 Containing 5.9% of Azadirachtin

Extract 1, 25 grams (g), containing 5.1% azadirachtin was dissolved in 140 g of ethyl acetate. To this solution, 30 g of saturated sodium bicarbonate solution and then 6 g of 30% hydrogen peroxide were added and the mixture was stirred for 45 minutes at 45 to 50° C. and then at 55° C. for 15 minutes. After phase separation, the upper organic phase was washed with brine containing a small amount of sodium bisulfite. Thereafter, the upper organic phase was separated, dried over magnesium sulfate, filtered, evaporated under reduced pressure and dried to yield 20 g of Extract 2 containing 5.9% azadirachtin.

EXAMPLE 3

Preparation of Extract 3 Containing 7.6% of Azadirachtin

Extract 2, 2 g, was stirred with 20 g of hexane for one hour and then filtered. The filter cake was dried overnight under reduced pressure to yield Extract 3 containing 7.6% azadirachtin.

EXAMPLE 4

Preparation of Extract 4 Containing 31% of Azadirachtin

Neem seeds, 3200 kg, were partially dehulled and then deoiled by standard methodology using mechanical oil extrusion followed by hexane extraction. The fully deoiled neem cake, 1400 kg, was ground in 7000 kg of methanol. After removal of all solids, the clear methanolic extract was concentrated to 366 kg. To this concentrate, 596 kg of water was added with stirring and, after 30 minutes, the resulting precipitate filtered off. The clear liquid phase was diluted with 1080 kg of brine and extracted with 571.5 kg of ethyl acetate. The extraction was then repeated with 202 kg of ethyl acetate and the combined ethyl acetate phases were evaporated to give 31 kg of a concentrate. To this concentrate, 27 kg of saturated sodium bicarbonate solution containing 5.4 kg of 35% hydrogen peroxide was added and the mixture was stirred and brought up to 55° C. After 30 minutes at 55° C., the mixture was allowed to reach room temperature, the phases were separated and the upper organic phase was dried over sodium sulfate, filtered and evaporated to yield 12.8 kg of Extract 4 containing 31% azadirachtin.

EXAMPLE 5

Preparation of Wettable Powders

Wettable powders (WP) containing stabilized extracts of this invention were prepared as follows:

| a. 20 WP | |
|---|---|
| Ingredients | Composition % by Weight |
| Stabilized extract (30% azadirachtin) | 66.6 |
| Sellogen ® DFL[1] | 2.0 |
| Tamol ® 731[2] | 5.0 |
| HiSil ® 233[3] | 26.4 |
| | 100.0 |

[1]Modified alkylnaphthalene sulfonate from Rhone-Poulenc
[2]Sodium salt of carboxylated polyelectrolyte from Rohm and Haas
[3]Silica from PPG The formulation was pulverized with a hammer-mill through a 0.020 inch screen followed by air milling to an average particle size of 3 millimicrons to give a wettable powder. The wetting time for 2 g in water of 342 ppm hardness as calcium carbonate was 50 seconds. The suspensibility in 342 ppm water at 1% concentration was 94% after 30 minutes.

| b. 75 WP | |
|---|---|
| Ingredients | Composition % by Weight |
| Stabilized extract (80% azadirachtin) | 93.8 |
| Aerosol ® OTB[1] | 1.0 |
| Morwet ® D425[2] | 5.2 |
| | 100.0 |

[1]Dioctyl sodium sulfosuccinate from American Cyanamid
[2]Sodium naphthalene formaldehyde condensate from DeSoto, Inc.

The formulation was processed essentially as described in Example 5a to give a wettable powder with similar physical properties and efficacy as an insecticide for foliar pests.

| c. 5 WP | |
|---|---|
| Ingredients | Composition % by Weight |
| Stabilized extract (20% azadirachtin) | 25.0 |
| Triton ® X-120[1] | 0.5 |
| Toranil B[2] | 1.0 |
| Barden ® Clay[3] | 73.5 |
| | 100.0 |

[1]Octyl polyethoxyethanol on carrier from Union Carbide
[2]Calcium lignosulfate from Rhinelander Paper
[3]Kaolin clay from Huber The formulation was processed essentially as described in Example 5a to give a wettable powder with similar physical properties and efficacy as an insecticide for foliar pests.

EXAMPLE 6

Stability Data and Sulfur Content

The extracts from Examples 1–4 and the 20 WP from Example 5a were analyzed for azadirachtin content and sulfur and then placed in an oven at 54° C. They were analyzed for azadirachtin again after 14 and 28 days.

Azadirachtin content in the examples was determined by reverse phase HPLC using a sample of pure azadirachtin as a standard.

The results obtained are as shown:

| Test Substance from Example | % Azadirachtin Content | | | % Azadirachtin Decomposition at Day 28 | Ppm of Sulfur Content[1] |
|---|---|---|---|---|---|
| | Day 0 | Day 14 | Day 28 | | |
| 1 | 5.1 | 1.3 | 0.0 | 100 | 6000 |
| 2 | 5.9 | 4.4 | 3.0 | 49 | 4200 |
| 3 | 7.6 | 6.6 | 5.7 | 25 | 4100 |
| 4 | 31.0 | 27.0 | 26.0 | 16 | 1500 |
| 5a | 20.0 | 18.0 | 18.0 | 10 | NA[2] |

[1]Initial measurement (Day 0)
[2]Not analyzed

EXAMPLE 7

Biological Activity

After storage for 28 days at 0° C. and 54° C., the extracts from examples 1, 2 and 4 and the 20 WP from Example 5a were tested for biological activity.

For the test, lima bean (*Phaseolus limensis* var. Woods' Prolific) plants, 2–3 weeks old, were sprayed to run-off with the test solution. After drying, the treated leaves were detached and infested with second instar larvae of Southern Armyworms (*Spodoptera eridania*) at doses of 150, 38, 10 and 2.5 ppm using 10 insects/dose. The percent mortality was determined at 3 days and at 6 days.

The results obtained are as shown:

| Test Substance from Ex. | 28-Day Storage Temp. °C. | % MORTALITY RESPONSE | | | | | | | |
|---|---|---|---|---|---|---|---|---|---|
| | | 3-DAY | | | | 6-DAY | | | |
| | | 150 | 38 | 10 | 2.5 | 150 | 38 | 10 | 2.5 |
| 1 | 0 | 90 | 80 | 10 | 10 | 100 | 100 | 100 | 10 |
| | 54 | 20 | 0 | 0 | 0 | 30 | 0 | 0 | 0 |
| 2 | 0 | 90 | 60 | 20 | 0 | 100 | 100 | 100 | 0 |
| | 54 | 100 | 40 | 0 | 0 | 100 | 100 | 20 | 0 |
| 4 | 0 | 90 | 70 | 30 | 0 | 100 | 100 | 10 | 10 |
| | 54 | 90 | 80 | 20 | 0 | 100 | 100 | 0 | 0 |
| 5a | 0 | 100 | 80 | 20 | 10 | 100 | 100 | 100 | 0 |
| | 54 | 100 | 100 | 20 | 10 | 100 | 100 | 100 | 20 |

It should be understood that the instant specification and examples are set forth by way of illustration and not limitation and that various modifications and changes may be made without departing from the spirit and scope of the present invention as defined by the appended claims.

I claim:

1. A process for purifying crude neem seed extracts to yield extracts useful as insecticides containing azadirachtin possessing less than 6000 ppm of sulfur and which degrades to an extent of less than 50% after 28 days at 54° C. comprising
   a) deoiling ground neem seeds, neem kernels or partially dehulled seeds by stirring with hexane followed by filtration to obtain a deoiled cake or by mechanically extruding the oil and optionally extruding the oil residue with hexane to obtain a deoiled cake,
   b) extracting the deoiled cake with methanol followed by filtration,
   c) removing the methanol to obtain a dry extract,
   d) dissolving about 3 parts of the dry extract in about 7 parts of methanol (w/w),
   e) adding water to a final ratio of about 35/65 methanol/water (v/v),
   f) separating the aqueous methanolic phase from any solid impurities,
   g) diluting the aqueous methanolic mixture with an aqueous salt solution,
   h) extracting the dilute solution with a water immiscible solvent,
   i) drying the resulting organic solution and, if desired, removing the solvent, and
   j) treating the resulting neem seed extract with an oxidizing agent.

2. A process for purifying crude neem seed extracts to yield extracts useful as insecticides containing azadirachtin possessing less than 6000 ppm of sulfur and which degrades to an extent of less than 50% after 28 days at 54° C. comprising
   a) evaporating a solution of crude neem seed extract in methanol to a concentrate containing over 65% volatiles,
   b) adding water dropwise with stirring to a final ratio of between 5/95 methanol/water (v/v) to 45/55 methanol/water (v/v),
   c) separating the resulting liquid aqueous methanolic phase from any solid impurities,
   d) diluting the resulting aqueous methanolic mixture with an aqueous salt solution,
   e) extracting the dilute solution with a water immiscible solvent,
   f) drying the resulting organic solution and, if desired, removing the solvent, and
   g) treating the resulting neem seed extract with an oxidizing agent.

3. The process of claim 2 wherein the final ratio of methanol/water (v/v) in step b is about 35/65.

4. The process of claim 1 or 2 wherein the water immiscible solvent is ethyl acetate.

5. The process of claim 1 or 2 wherein the oxidizing agent is an alkaline solution of hydrogen peroxide.

6. The process of claim 5 wherein the alkaline solution is a sodium bicarbonate solution.

7. A storage stable neem seed extract prepared by the process of claims 1 or 2 wherein no more than 25% of the azadirachtin contained in the extract decomposes after storage at 54° C. for 28 days.

8. An insecticidal composition which comprises an agronomically acceptable carrier and an insecticidally effective amount of the extract of claim 7.

9. The extract of claim 8 wherein said extract is formulated as a wettable powder.

10. A neem seed extract useful as an insecticide which contains azadirachtin with enhanced stability and less than 4200 ppm of sulfur.

* * * * *